(12) United States Patent
Jager Lezer

(10) Patent No.: US 6,689,345 B2
(45) Date of Patent: Feb. 10, 2004

(54) CARE OR MAKE-UP COMPOSITION CONTAINING FIBERS AND A HYDROPHILIC POLYOGANOSILOXANE

(75) Inventor: Nathalie Jager Lezer, Bourg la Reine (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/251,856

(22) Filed: Sep. 23, 2002

(65) Prior Publication Data

US 2003/0031642 A1 Feb. 13, 2003

Related U.S. Application Data

(63) Continuation of application No. 09/607,627, filed on Jun. 30, 2000.

(30) Foreign Application Priority Data

Jul. 1, 1999 (FR) ............................................. 99 08489

(51) Int. Cl.$^7$ ................................................ A61K 7/025
(52) U.S. Cl. ........................... 424/64; 424/63; 424/401; 424/78.02; 424/78.03; 424/489; 424/500; 424/501; 424/502
(58) Field of Search ........................... 424/401, 64, 65, 424/70.1, 70.7, 63, 78.02, 78.03, 489, 500, 501, 502

(56) References Cited

U.S. PATENT DOCUMENTS

| | | | |
|---|---|---|---|
| 5,965,146 A | 10/1999 | Franzke et al. | 424/401 |
| 6,030,630 A | * 2/2000 | Fleury et al. | 424/401 |
| 6,057,386 A | 5/2000 | Morita et al. | 523/212 |

FOREIGN PATENT DOCUMENTS

| | | |
|---|---|---|
| EP | 0 293 795 | 12/1988 |
| EP | 0 295 886 | 12/1988 |

OTHER PUBLICATIONS

Morrison, R.T. and Boyd, R.N. Organic Chemistry, Fourth Edition. Allyn and Bacon, Inc. Boston, London, Sydney, Toronto. 1983.*

* cited by examiner

Primary Examiner—Thurman K. Page
Assistant Examiner—Liliana Di Nola-Baron
(74) Attorney, Agent, or Firm—Oblon, Spivak, McClelland, Maier & Neustadt, P.C.

(57) ABSTRACT

A care or make-up composition for keratin substances such as the skin, the lips or superficial body growths, this composition containing fibers and particles of an at least partially crosslinked solid elastomeric polyorganosiloxane suspended in an aqueous phase, giving a homogeneous deposit on these keratin substances, while at the same time providing softness and a sensation of freshness; methods of using the composition; and methods of making the composition.

63 Claims, No Drawings

CARE OR MAKE-UP COMPOSITION CONTAINING FIBERS AND A HYDROPHILIC POLYOGANOSILOXANE

BACKGROUND OF THE INVENTION

1. Field of the Invention

The present invention relates to a composition containing fibers and an aqueous dispersion of a polyorganosiloxane, this composition being intended for cosmetics and dermatology. More especially, the invention applies to the care and/or treatment and/or making up of keratin substances or surfaces such as the skin, including the scalp, the facial lips and superficial body growths such as the eyelashes, the eyebrows, the nails and the hair of human beings. This composition feels soft and fresh when applied, spreads easily, is non-sticky and does not dry out the skin or the lips. It is perfectly suitable for greasy skin, on account of its great matt-effect power.

This composition can be in particular in the form of a product cast as a stick or a dish, such as lipsticks or lip balms, cast foundations, concealer products, deodorants, eyeshadows or face powders; in the form of a more or less fluid paste or cream, such as fluid foundations or lipsticks, eyeliners, mascaras, care, antisun or colouring compositions for the skin, make-up compositions for the body or make-up compositions for the nails and the hair; or in the form of an aqueous gel, such as treating shampoos.

2. Description of the Background

It is known practice to use fibers in make-up products, in particular for their lengthening effects in mascaras (see JP-A-57/158 714), their "textile" feel (see JP-A-7/196 440), their fabric effect or their moisturizing properties in lipsticks (see U.S. Pat. No. 5,498,407) or for improving the contours of the lipstick on the edges of the lips (see EP-A-0 106 762). Unfortunately, it is very difficult to disperse fibers in compositions homogeneously and without forming lumps, which, in a coloured composition and in particular a make-up, generally gives a non-uniform and relatively unaesthetic make-up result whose contour is not particularly sharp. In addition, this difficulty of dispersion gives compositions whose cosmetic properties are not constant and difficult to reproduce, thus entailing problems of industrial manufacture and high manufacturing costs.

Make-up or care products for the skin or the lips of human beings, such as foundations or lipsticks, generally contain fatty phases such as waxes and oils, pigments and/or fillers and optionally additives such as cosmetic or dermatological active agents. The fillers generally serve to modify the texture of the composition and in particular to rigidify it as well as to give a matt effect to the film of composition deposited on the skin and/or the lips, which is particularly desired for users with combination or greasy skin, as well as for users in hot and humid climates. On the other hand, the pigments generally serve to bring colour to the composition. Unfortunately, the fillers used to give a matt effect do not give the skin a fresh sensation, but rather a sensation of dryness as well as tautness and discomfort.

There is thus a need for a composition which does not have the above drawbacks, and in particular which does not dry out the skin or the lips onto which it is applied, either during the application or over time, and which gives a homogeneous, aesthetic care or make-up effect and a sensation of freshness, while at the same time giving a matt effect.

SUMMARY OF THE INVENTION

An object of the invention is, precisely, a care and/or treatment and/or make-up composition for keratin substances which overcomes these drawbacks. The Applicant has found, surprisingly, that the use of fibers and an aqueous dispersion of partially crosslinked polyorganosiloxane in a make-up composition gives the composition good cosmetic properties, and in particular gives a homogeneous, uniform make-up result with sharp contours when applied, accompanied by a soft feel and a sensation of freshness. This make-up is also comfortable to wear throughout the day and has matt-effect and water-resistance properties.

The invention applies not only to make-up products for the skin, both of the human face and body, and for the facial lips, but also to make-up products for superficial body growths such as the eyelashes, eyebrows, nails and hair, as well as to care and/or treatment products for the skin, including the scalp.

DETAILED DESCRIPTION OF THE INVENTION

More specifically, an object of the invention is a care or make-up composition for keratin substances, containing an aqueous phase, particles of an at least partially crosslinked solid elastomeric polyorganosiloxane and fibers dispersed in the aqueous phase.

In particular, the polyorganosiloxane particles and the fibers are dispersed or even dissolved directly in the aqueous phase.

An object of the invention is also a cosmetic care or treatment process for keratin substances, and in particular the skin or the lips of human beings, comprising the application to these keratin substances of the composition, in particular the cosmetic composition, as defined above.

An object of the invention is also the cosmetic use of particles of an at least partially crosslinked solid elastomeric polyorganosiloxane suspended in an aqueous phase, combined with fibers, in a cosmetic composition in particular for caring for or making up keratin substances or for the manufacture of a composition for topical application and more especially a make-up or care composition for keratin substances, which is water-resistant and/or which gives a homogeneous and/or fresh and/or matt make-up or care result.

The term "fiber" should be understood as being an object of length L and diameter D such that L is very much greater than D, D being the diameter of the circle in which the cross section of the fiber is inscribed. In particular, the ratio L/D (or shape factor) is chosen within the range from 3.5 to 2500, preferably from 5 to 500 and better still from 5 to 150.

The aqueous phase advantageously contains water and optionally one or more compounds that are at least partially miscible with water, such as polyols, lower $C_2$ to $C_5$ monoalcohols and $C_3$ to $C_4$ ketones that are liquid at room temperature.

The term "room temperature" should be understood as being a temperature of 25° C., at normal atmospheric pressure (760 mmHg).

The term "polyol" should be understood as being any organic molecule comprising at least two free hydroxyl groups. In particular, the polyol(s) of the invention has (have) an IOB (inorganic/organic balance) value of greater than 0.5 and in particular ranging from 1 to 7 and more especially from 1.5 to 5.5. These polyols serve in particular as fiber-wetting agents.

The IOB parameter is known to those skilled in the art from a certain number of publications such as the article by A. Fujita, Pharm. Bull 2, 163–173 (1954) and documents J09/151 109 and J08/217 639 from Shiseido or J09/175 925 from Kose.

As examples of polyols which satisfy the above criteria and which can be used, alone or as a mixture, in the composition of the invention, mention may be made of:

| Name | IOB value |
|---|---|
| Propylene glycol | 3.333 |
| Butylene glycol | 2.500 |
| Isoprene glycol | 2.222 |
| Pentylene glycol | 2.000 |
| Hexylene glycol | 1.818 |
| PEG-4 (*) | 2.656 |
| PEG-6 | 2.396 |
| PEG-8 | 2.266 |
| Glycerol | 5.000 |
| Panthenol | 3.125 |

(*) In general, mention may be made of polyethylene glycols (PEG) containing from 4 to 8 ethylene glycol units.

The aqueous phase can represent from 1% to 98% relative to the total weight of the composition and preferably from 10% to 95% and better still from 30% to 95%.

The water-miscible compound(s) can be present in an amount ranging from 0% to 30% relative to the total weight of the composition, in particular from 0.1% to 30% and better still in an amount ranging from 1% to 15%.

This composition in particular feels non-sticky, non-greasy and soft when applied and spreads well, while at the same time being of uniform appearance.

The fibers which can be used in the composition of the invention can be fibers of synthetic or natural, mineral or organic origin. They can be short or long, individual or organized for example in plaits, and hollow or solid. They can be of any shape and in particular of circular or polygonal (square, hexagonal or octagonal) cross section depending on the specific application envisaged. In particular, their ends are blunt and/or polished in order to prevent injury.

In particular, the fibers have a length ranging from 1 nm to 20 mm, preferably from 0.1 mm to 5 mm and better still from 0.2 mm to 1.6 mm. Their cross section can be within a circle of diameter ranging from 2 nm to 100 $\mu$m, preferably ranging from 20 nm to 50 $\mu$m and better still from 500 nm to 50 $\mu$m. The weight of the fibers or yarn count is often given in denier or decitex and represents the weight in grams of 9 km of yarn. The fibers according to the invention preferably have a yarn count chosen within the range from 0.15 denier to 30 denier and better still from 0.18 denier to 18 denier.

In order to obtain a glossy make-up, which is most particularly desired for making up the nails and the lips, short fibers in particular having a length ranging from 1 nm to 200 $\mu$m are advantageously used. On the other hand, for a matt make-up, which is especially desired for making up the face (in particular for a powder or a foundation), long fibers in particular having a length of greater than 200 $\mu$m are preferably used.

The fibers can be those used in the manufacture of textiles, and in particular silk fiber, cotton fiber, wool fiber, flax fiber, cellulose fibers extracted in particular from wood, from plants or from algae, polyamide (Nylon®) fiber, rayon fiber, viscose fiber, acetate fiber, in particular silk, cellulose or rayon acetate fiber, poly(p-phenyleneterephthamide) fiber, in particular Kevlar®, acrylic fiber, in particular polymethyl methacrylate fiber or poly(2-hydroxyethyl methacrylate) fiber, polyolefin fiber and in particular polyethylene or polypropylene fiber, glass fiber, silica fiber, aramide fiber, carbon fiber, in particular in graphite form, polytetrafluoroethylene (Teflon®) fiber, insoluble collagen fiber, polyester fiber, polyvinyl chloride fiber or polyvinylidene chloride fiber, polyvinyl alcohol fiber, polyacrylonitrile fiber, chitosan fiber, polyurethane fiber, polyethylene phthalate fiber, and fibers formed from a mixture of polymers such as those mentioned above, for instance polyamide/polyester fibers.

The fibers used in surgery can also be used, for instance resorbable synthetic fibers prepared from glycolic acid and ε-caprolactone (Monocryl from Johnson & Johnson); resorbable synthetic fibers of the type which is a copolymer of lactic acid and of glycolic acid (Vicryl from Johnson & Johnson); polyterephthalic ester fibers (Ethibond from Johnson & Johnson) and stainless steel threads (Acier from Johnson & Johnson), in particular for an application in nail varnish.

Moreover, the fibers may be treated or untreated at the surface, and coated or uncoated. As coated fibers which can be used in the invention, mention may be made of polyamide fibers coated with copper sulphide for an antistatic effect (for example R-STAT from Rhodia) or another polymer allowing a particular organization of the fibers (specific surface treatment) or a surface treatment which induces colour/hologram effects (Lurex fiber from Sildorex, for example).

Fibers of synthetic origin are preferably used, and in particular organic fibers, such as those used in surgery.

The fibers which can be used in the composition according to the invention are preferentially polyamide fibers or poly(p-phenyleneterephthamide) fibers. Their length L can range from 0.1 mm to 5 mm, preferably from 0.25 mm to 1.6 mm, and their average diameter D can range from 5 $\mu$m to 50 $\mu$m. In particular, the polyamide fibers sold by Etablissements P. Bonte under the name Polyamide 0.9 Dtex 0.3 mm can be used, having an average diameter of 6 $\mu$m, 12.2 $\mu$m or 20 $\mu$m, a weight of about (0.9 dtex) and a length ranging from 0.3 mm to 1 mm. Poly(p-phenyleneterephthamide) fibers with an average diameter of 12 $\mu$m and a length of about 1.5 mm can also be used, such as those sold under the name Kevlar Floc by the company Du Pont Fibers.

The concentration of fibers depends on the specific application and on the type of product envisaged. For a make-up product for the face such as a foundation, or for the lips (such as a lipstick), the concentration of fibers can range from 0.1% to 20% relative to the total weight of the composition, preferably from 0.5% to 10%. For a special effect, in particular a make-up effect for the body, the nails or the hair, the amount of fibers can range up to 30% relative to the total weight of the composition.

The composition of the invention can be in the form of a paste, a solid, a more or less fluid cream or even a lotion. It can be an aqueous or hydrophilic gel, a fluid, rigid or soft oil-in-water or water-in-oil dispersion or emulsion, optionally cast as a stick or a dish.

The term "elastomeric" polyorganosiloxane means a soft, deformable polyorganosiloxane which has viscoelastic properties and in particular the consistency of a sponge or a soft sphere. Its modulus of elasticity is such that this material is resistant to deformation and has a limited capacity for extension and contraction. This material is capable of regaining its original shape after it has been stretched. This elastomer is formed from polymer chains of high molecular weight whose mobility is limited by a uniform network of crosslinking points.

The elastomeric polyorganosiloxanes in the composition of the invention have aqueous-medium-structuring properties and are capable of increasing the viscosity of this aqueous medium, in addition to good cosmetic properties, in particular softness, a sensation of freshness and a matt effect. They do not dry out the skin. These novel elastomers give compositions that are comfortable when applied, spread well and feel soft and non-sticky. These cosmetic properties are due partly to the texture of the polyorganosiloxanes and partly to their properties comparable to those of microsponges trapping the aqueous media and in particular those of the composition and those due to perspiration of the skin. When combined with the fibers, they give more or less thickened compositions which have good remanence with respect to water and good stability.

The elastomeric polyorganosiloxanes in accordance with the invention are partially or totally crosslinked hydrophilic compounds of three-dimensional structure. The thickening of the aqueous phase with these elastomers can be total or partial. It is entirely surprising that hydrophilic polymers combined with fibers should have properties of remanence with respect to water.

The elastomers in the composition of the invention are in the form of a powder or an emulsified gel containing an elastomeric polyorganosiloxane of three-dimensional structure, dispersed in water. The dispersion (or suspension) of the particles is homogeneous.

The elastomeric polyorganosiloxanes according to the invention can be chosen from the crosslinked polymers described in patent application JP-A-10/175 816. According to this application, they are obtained by addition reaction and crosslinking, in the presence of a catalyst in particular of platinum type, of at least:

(a) one polyorganosiloxane (i) containing at least two vinyl groups in $\alpha$-$\Omega$ position of the silicone chain per molecule; and (b) one organosiloxane (ii) containing at least one hydrogen atom linked to a silicon atom per molecule.

In particular, the polyorganosiloxane (i) is chosen from polydimethylsiloxanes and is more specifically an $\alpha,\Omega$-dimethylvinyl polydimethylsiloxane.

The elastomeric polyorganosiloxanes in the composition according to the invention are advantageously in the form of an aqueous suspension or dispersion. This suspension can be obtained in particular as follows:

(a) mixing the polyorganosiloxane (i) and the organosiloxane (ii);

(b) adding the aqueous phase containing an emulsifier to the mixture from step (a);

(c) emulsifying the aqueous phase and the said mixture;

(d) adding hot water to the emulsion from step (c); and (e) polymerizing the polyorganosiloxane (i) and the organosiloxane (ii) in emulsion in the presence of a platinum catalyst.

The water is advantageously added at a temperature of 40–60° C. After step (e), it is possible to dry the particles obtained in order to evaporate therefrom all or some of the water trapped.

The polyorganosiloxanes are in the form of hydrophilic deformable solid particles having a certain level of hardness, which can be measured using a Shore A durometer (according to ASTM standard D2240) at room temperature or by the Japanese method JIS-A. This hardness can be measured on a block of elastomer prepared for this purpose, as follows: mixing the polyorganosiloxane (i) and the organosiloxane (ii); removing the air from the mixture; moulding and vulcanizing in an oven at 100° C. for 30 minutes; cooling to room temperature and then measuring the hardness. The density is also determined on this block of elastomer.

In particular, the Shore hardness can range from 1 to 100 and is advantageously less than or equal to 80 and better still less than 65, for example between 5 and 50 (limits included).

The polyorganosiloxanes in the composition of the invention are, for example, those sold under the names BY 29-122 and BY 29-119 from the company Dow-Corning Toray. A mixture of these commercial products can also be used.

A block of elastomer according to the product BY 29-119 has a hardness of 30 and according to the product BY 29-122, a hardness of 7. The density is from 0.97 to 0.98.

The elastomeric polyorganosiloxane powder is preferably present in the composition in a content of from 0.1% to 70%, preferably 4% to 70% and better still from 4% to 50%, which corresponds to an active material content in the polymer of from 0.5% to 65% by weight and better still from 3% to 45%. It in fact constitutes a water-dispersible filler.

The particles of elastomeric polyorganosiloxane (as active material) in particular have a size ranging from 0.1 $\mu$m to 500 $\mu$m, preferably from 3$\mu$m to 200 $\mu$m and better still from 10 $\mu$m to 20 $\mu$m. These particles can be spherical, flat or amorphous, preferably with a spherical shape. The size of the particles in the product BY 29-119 and in the product BY 29-122 is 4.5 $\mu$m.

In order to be stably dispersed in water, these polyorganosiloxane particles can be combined with one or more nonionic, cationic or anionic surfactants of HLB $\geq$ 8. Step (c) is obtained in particular in the presence of a nonionic emulsifier.

The proportion of surfactants is preferably from 0.1 to 20 parts by weight per 100 parts by weight of elastomeric polyorganosiloxane, and better still from 0.5 to 10 parts by weight (cf. description in JP-A-10/175 816).

The dispersion of elastomeric polyorganosiloxane powder and fibers can be combined with a fatty phase containing one or more fatty substances that are liquid at room temperature, known as oils, such as those described in JP-A-10/175 816, one or more waxes or one or more gums that are solid at room temperature, one or more pasty fatty substances of animal, plant, mineral or synthetic origin, mixtures thereof and inorganic powders or fillers such as those described in the said document.

This additional fatty phase can be of any nature and can contain in particular products that are fluid at room temperature and atmospheric pressure, known as oils, such as silicone oils, fluoro oils, fluorosilicone oils and optionally partially silicone-containing hydrocarbon-based oils. These oils can be of animal, plant, mineral or synthetic origin. These oils can be volatile at room temperature and atmospheric pressure. The term "volatile oil" in particular means an oil which can evaporate, in less than one hour, on contact with the skin or the lips.

The term "fatty phase" should be understood as meaning a non-aqueous, water-immiscible medium containing one or more fatty substances chosen from compounds containing at least 10 carbon atoms and better still 16 carbon atoms, silicone compounds and fluoro compounds, and mixtures thereof. The organic solvents conventionally used in nail varnishes are not considered as fatty substances.

The term "hydrocarbon-based oil" means an oil mainly containing carbon atoms and hydrogen atoms and in particular alkyl or alkenyl chains, such as alkanes or alkenes, but also an oil containing an alkyl or alkenyl chain comprising one or more ether, ester or carboxylic acid groups.

As oils which can be used in the composition of the invention, mention may be made in particular of:

hydrocarbon-based oils of animal origin, such as perhydrosqualene;

hydrocarbon-based plant oils such as liquid triglycerides of fatty acids of 4 to 10 carbon atoms, such as heptanoic or octanoic acid triglycerides or alternatively, for example, sunflower oil, corn oil, soybean oil, marrow oil, grapeseed oil, sesame oil, hazelnut oil, apricot oil, macadamia oil, arara oil, castor oil, avocado oil, caprylic/capric acid triglycerides such as those sold by the company Stearineries Dubois or those sold under the names Miglyol 810, 812 and 818 by the company Dynamit Nobel, jojoba oil or Karite butter;

synthetic esters and ethers in particular of fatty acids, such as the oils of formula $R^1COOR^2$ in which $R^1$ represents a higher fatty acid residue containing from 7 to 29 carbon atoms and $R^2$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate, and fatty alkyl heptanoates, octanoates and decanoates; polyol esters such as propylene glycol dioctanoate, neopentyl glycol diheptanoate or diethylene glycol diisononanoate; and pentaerythiritol esters such as pentaerythrityl tetraisostearate;

linear or branched hydrocarbons of mineral or synthetic origin, such as volatile or non-volatile liquid paraffins and derivatives thereof, petroleum jelly, polydecenes or hydrogenated polyisobutene such as parleam;

synthetic esters and ethers such as isopropyl myristate and alkyl or polyalkyl octanoates, decanoates or ricinoleates;

fatty alcohols containing from 12 to 26 carbon atoms, such as octyldodecanol, 2-butyloctanol, 2-hexyldecanol, 2-undecylpentadecanol or oleyl alcohol;

partially hydrocarbon-based and/or silicone-based fluoro oils such as those described in JP-A-2 295 912;

silicone oils such as volatile or non-volatile polydimethylsiloxanes (PDMSs) containing a linear or cyclic silicone chain, which are liquid or pasty at room temperature;

polydimethylsiloxanes comprising alkyl, alkoxy or phenyl groups, pendant or at the end of a silicone chain, these groups containing from 2 to 24 carbon atoms; phenylsilicones such as phenyl trimethicones, phenyl dimethicones, phenyltrimethylsiloxydiphenylsiloxanes diphenyl dimethicones, diphenylmethyldiphenyltrisiloxanes, 2-phenylethyl trimethylsiloxysilicates and polymethylphenylsiloxanes;

mixtures thereof.

These oils can represent from 0% to 98.80% relative to the total weight of the composition, preferably from 0.5% to 80% and better still from 1% to 70%.

The composition according to the invention can advantageously contain agents for structuring the liquid fatty phase, such as waxes, gums and fillers. The waxes can be hydrocarbon-based (containing only carbon and hydrogen atoms), fluoro waxes and/or silicone waxes or mixtures thereof, which may be solid or semi-solid (in the form of a paste) at room temperature and which may optionally comprise ester, hydroxyl or thiol functions. These waxes in particular have a melting point of greater than 45° C.

The silicone waxes can be waxes comprising a silicone structure and units containing one or more alkyl or alkoxy chains pendant and/or at the end of a silicone structure, these chains being linear or branched and containing from 10 to 45 carbon atoms. These waxes are known, respectively, as alkyl dimethicones and alkoxy dimethicones. These alkyl chains can moreover comprise one or more ester functions.

As other waxes which can be used in the invention, mention may be made of waxes of animal origin such as lanolin or beeswax; waxes of plant origin such as carnauba wax or candelilla wax; waxes of mineral origin, for example paraffin wax, lignite wax or microcrystalline waxes, ceresin or ozokerite; synthetic waxes such as polyethylene waxes and Fischer-Tropsch waxes, and mixtures thereof.

These fatty substances can be chosen in a varied manner by a person skilled in the art in order to prepare a composition having the desired properties, for example in terms of consistency or texture.

The presence of waxes in particular ensures good mechanical strength, especially when the composition is in the form of a stick.

The composition can generally comprise from 0% to 50% of wax relative to the total weight of the composition, and preferably from 5% to 30%.

The composition of the invention can also comprise any additional additive usually used in the field under consideration, such as dyestuffs, for instance pigments, nacres, water-soluble or liposoluble dyes, antioxidants, essential oils, preserving agents, cosmetic or dermatological active agents such as emollients, moisturizers (glycerol), vitamins, essential fatty acids, liquid lanolin, lipophilic or hydrophilic sunscreens, liposoluble polymers, in particular hydrocarbon-based polymers such as polyalkylenes, neutralizing agents, agents for gelling or thickening a liquid fatty phase, and fragrances, and mixtures thereof.

These additives can be present in the composition in the amounts usually used and, for example, in a proportion of from 0% to 20% relative to the total weight of the composition, and better still from 0.1% to 10%.

The composition of the invention advantageously contains as additional additive one or more aqueous-phase thickeners or gelling agents. Among the aqueous-phase gelling agents which can be used according to the invention, mention may be made of: water-soluble cellulosic gelling agents such as hydroxyethylcellulose, methylcellulose, hydroxy-propylcellulose or carboxymethylcellulose; guar gum; quaternized guar gum; nonionic guar gums comprising $C_1$–$C_6$ hydroxyalkyl groups; xanthan gum, carob gum, scleroglucan gum, gellan gum, rhamsan gum or karaya gum; alginates, maltodextrin, starch and its derivatives, and hyaluronic acid and its salts; clays and in particular montmorillonites, hectorites or bentones, and laponites; polymers containing a carboxylic group, for instance crosslinked, at least partially neutralized polyacrylic acids such as the "Carbopol" or "Carbomer" products from the company Goodrich (Carbomer 980, for example neutralized with triethanolamine—abbreviated as TEA); polyglyeryl (meth)acrylate polymers; polyvinylpyrrolidone; polyvinyl alcohol; crosslinked acrylamide polymers and copolymers; crosslinked methacryloyloxyethyltrimethylammonium chloride homopolymers; associative polyurethanes, and mixtures thereof. These gelling agents can represent from 0% to 60% relative to the total weight of the composition, and in particular from 0.1% to 50%.

According to the invention, the aqueous-phase gelling agent is preferably chosen from xanthan gum, clays (bentone or laponite), associative polyurethanes, cellulosic thickeners, in particular hydroxyethylcellulose, and crosslinked, at least partially neutralized polyacrylic acids.

It is within the routine skill of a person skilled in the art to select the optional additional additives and/or the amount thereof such that the advantageous properties of the composition according to the invention are not, or are not substantially, adversely affected by the addition envisaged. In particular, these additives must not be harmful to the homogeneity, stability, comfort, matt effect, freshness or water-resistance of the composition.

The composition according to the invention can be in the form of a coloured product and especially coloured make-up product for the skin, in particular a foundation, a blusher, a face powder, an eyeshadow, a mascara, an eyeliner, a concealer product in stick form, a nail varnish or a make-up product for the lips such as a lipstick or lip gloss, optionally having care or treatment properties, or a body tattoo. They can also be in uncoloured form, optionally containing cosmetic or dermatological active agents. In this case, they can be used as a care base for the lips (lip balms for protecting the lips against the cold and/or sunlight and/or the wind) or a fixing base to be applied over a conventional lipstick.

The composition of the invention can also be in the form of a dermatological or cosmetic treatment or care composition for the skin (including the scalp), keratin fibers (hair, eyelashes, eyebrows), the nails or the lips or in the form of an antisun composition or artificial tanning composition, or alternatively in the form of a cleansing product or make-up-remover for the skin or keratin fibers, a deodorant product or a fragrancing product. In this case, it can be in uncoloured form, optionally containing cosmetic or dermatological active agents. It can thus be used as a care base for the skin or the lips (lip balm for protecting the lips against the cold and/or sunlight and/or the wind) or a day or night care cream. It can also be in the form of a treating or non-treating, colouring or non-colouring shampoo or a hair conditioner.

The composition of the invention should be cosmetically or dermatologically acceptable, i.e. it should contain a non-toxic physiologically acceptable medium which can be applied to the skin (including the inner edge of the eyelids) or the lips of the human face as well as to the superficial body growths of human beings.

The composition of the invention can preferably comprise a dyestuff in particular containing a particulate phase, which is generally present in a proportion of from 0% to 60% relative to the total weight of the composition, preferably from 5% to 35%, and which can comprise pigments and/or nacres and/or fillers usually used in cosmetic compositions. The dyestuff can also consist of dyes that are soluble in the medium, and in particular lipophilic or hydrophilic dyes such as Sudan red or brown, methylene blue, β-carotene or beetroot juice; they can represent from 0% to 6% relative to the total weight of the composition.

The term "pigments" should be understood as meaning white or coloured, mineral or organic particles which are insoluble in the medium of the composition and are intended to colour and/or opacify the composition. The term "fillers" should be understood as meaning colourless or white, mineral or synthetic, lamellar or non-lamellar particles. The term "nacres" should be understood as meaning iridescent particles, in particular produced by certain molluscs in their shell, or alternatively synthesized. These fillers and nacres serve to modify the texture of the composition as well as the matt/gloss effect.

The pigments can be present in the composition in a proportion of from 0% to 60% relative to the weight of the final composition, preferably in a proportion of from 0.05% to 25% and better still from 4% to 20%. As mineral pigments which can be used in the invention, mention may be made of titanium oxide, zirconium oxide or cerium oxide, as well as zinc oxide, iron oxide or chromium oxide and ferric blue. Among the organic pigments which can be used in the invention, mention may be made of carbon black and barium, strontium, calcium and aluminium lakes, and mixtures thereof.

The nacres can be present in the composition in a proportion of from 0% to 20% relative to the total weight of the composition, preferably in a content from about 1% to 15%. Among the nacres which can be used in the invention, mention may be made of mica coated with titanium oxide, with iron oxide, with natural pigment or with bismuth oxychloride, such as coloured titanium mica.

The fillers can be present in a proportion of from 0% to 35% relative to the total weight of the composition, preferably 0.5% to 15%. Mention may be made in particular of talc, mica, silica, Nylon® (in particular Orgasol® from Atochem) powder, polyethylene powder, Teflon®, starch, boron nitride, copolymer microspheres such as Expancel® (Nobel Industrie), Polytrap® (Dow Corning) and silicone resin microbeads (for example Tospearl® from Toshiba), and mixtures thereof.

The composition according to the invention can be manufactured with or without heating of one or more elastomeric polyorganosiloxanes in powder form dispersed in water, addition of one or more pigments, one or more fillers and/or one or more other additives, optional addition of the fatty phase in liquid form (in particular raised to the highest melting point of the waxes) and then emulsification, if necessary.

It can also be obtained by extrusion as described in patent application EP-A-667 146. This process consists in blending the paste (waxes+oils+additives+pigments) during the cooling in order to create zones in which the paste is crushed with the aid of a roll mill or a screw extruder-mixer. This product gives a composition in the form of a soft paste.

Having generally described this invention, a further understanding can be obtained by reference to certain specific examples which are provided herein for purposes of illustration only and are not intended to be limiting unless otherwise specified.

The percentages are given on a weight basis.

EXAMPLE 1

Foundation

| Oily phase | |
|---|---|
| Cyclopentasiloxane | 10% |
| KSG-21 | 20.4% |
| Pigments | 10% |
| Aqueous phase | |
| Trefil BY 29–119 | 5% |
| Xanthan | 0.3% |
| Polyamide fiber | 2.5% |
| Propylene glycol | 4% |
| Preserving agents | qs |
| Water | qs 100 |

Preparation:

The fibers are introduced at room temperature (25° C.) into the propylene glycol and the assembly is subjected to stirring at 1000 rpm for 30 min with a Rayneri turbomixer. Separately, the pigments are introduced into the oil/KSG 21 mixture, with stirring in a three-roll turbomixer. The propylene glycol/fiber mixture is introduced into the KSG 20/oil/pigment mixture.

A foundation is obtained which feels fresh when applied, is soft and easy to work, giving a homogeneous, uniform and aesthetic make-up effect.

EXAMPLE 2

Tinted Body Gel

| | |
|---|---|
| Trefil BY 29–119 | 32% |
| Carbomer 980 | 0.6% |
| Triethanolamine (neutralizing agent) | 0.6% |
| Polyamide fibers (0.3 mm long) | 1% |
| Propylene glycol | 1.8% |
| Pigments | 5% |
| Preserving agents | qs |
| Water | qs 100 |

Preparation:

This coloured cream-gel is prepared by adding the polyorganosiloxane to the water at room temperature, followed by adding the neutralized gelling agent and then the pigments and the preserving agents. In parallel, the fibers are introduced at room temperature into the propylene glycol and the mixture obtained is subjected to stirring at 1000 rpm for 30 min with a Rayneri turbomixer. Finally, the fibers/propylene glycol mixture is introduced into the polyorganosiloxane gel and the whole is then mixed by stirring with the Rayneri machine for 10 to 15 minutes. This gel is intended in particular for making up the body or for tattooing. It allows application onto small areas of the body, with a sharp contour. The film deposited is uniform. The gel gives a homogeneous, aesthetic, soft, non-greasy make-up effect, assessed by a panel of 6 individuals. This gel gives a very strong matt effect, a great sensation of freshness when applied, has good staying power over time and is water-resistant, unlike the products of the prior art.

The disclosure of France priority application 9908489, filed Jul. 1, 1999, is hereby incorporated by reference.

What is claimed is:

1. A make-up composition formulated for use on skin, lips or nails comprising a dyestuff and an aqueous phase, said aqueous phase comprising fibers and particles of an at least partially crosslinked solid elastomeric polyorganosiloxane dispersed therein.

2. The composition according to claim 1, wherein the elastomeric polyorganosiloxane is obtained by addition reaction and crosslinking, in the presence of a catalyst, of at least:

one polyorganosiloxane (i) containing at least two vinyl groups in α-Ω position of the silicone chain per molecule; and one organosiloxane (ii) containing at least one hydrogen atom linked to a silicon atom per molecule.

3. The composition according to claim 2, wherein the polyorganosiloxane (i) is selected from polydimethylsiloxanes.

4. The composition according to claim 3, wherein the polyorganosiloxane (i) is an α-Ω-dimethylvinyl polydimethylsiloxane.

5. The composition according to claim 2, wherein the dispersion of polyorganosiloxane particles is obtained according to the following steps:

(a) mixing the polyorganosiloxane (i) and the organosiloxane (ii);

(b) adding the aqueous phase containing an emulsifier to the mixture from step (a);

(c) emulsifying the aqueous phase and the said mixture;

(d) adding hot water to the emulsion from step (c); and (e) polymerizing the polyorganosiloxane (i) and the organosiloxane (ii) in emulsion in the presence of a platinum catalyst.

6. The composition according to claim 5, wherein step (c) is carried out in the presence of a nonionic emulsifier.

7. The composition according to claim 1, wherein the particles of elastomeric polyorganosiloxane have a size ranging from 0.1 82 m to 500 µm.

8. The composition according to claim 7, wherein the particles of elastomeric polyorganosiloxane have a size ranging from 3 µm to 200 µm.

9. The composition according to claim 1, wherein the polyorganosiloxane particles have a hardness of less than or equal to 80.

10. The composition according to claim 9, wherein the polyorganosiloxane particles have a hardness of less than 65.

11. The composition according to claim 1, wherein the elastomeric polyorganosiloxane is present in an amount of from 0.1% to 70% relative to the total weight of the composition.

12. The composition according to claim 11, wherein the elastomeric polyorganosiloxane is present in an amount of from 4% to 50%.

13. The composition according to claim 1, wherein the fibers are selected from the group consisting of silk fiber, cotton fiber, wool fiber, flax fiber, cellulose fibers polyamide fiber, rayon fiber, viscose fiber, acetate fiber, poly(p-phenyleneterephthamide) fiber, acrylic fiber, polyolefin fiber, glass fiber, silica fiber, aramide fiber, carbon fiber, Teflon® fiber, insoluble collagen fiber, polyester fiber, polyvinyl chloride fiber, polyvinylidene chloride fiber, polyvinyl alcohol fiber, polyacrylonitrile fiber, chitosan fiber, polyurethane fiber, polyethylene phthalate fiber, fibers from mixtures of polymers, and surgical fibers.

14. The composition according to claim 12, wherein the cellulose fibers are extracted from wood, from plants or from algae, the acrylic fiber is polymethyl methacrylate fiber or poly(2-hydroxyethyl methacrylate) fiber, the polyolefin fiber is polyethylene or polypropylene fiber, and the carbon fiber is in graphite form.

15. The composition according to claim 1, wherein the fibers are fibers of synthetic origin.

16. The composition according to claim 1, wherein the fibers are polyamide fibers or poly(p-phenyleneterephthamide) fibers.

17. The composition according to claim 1, wherein the fibers have a yarn count which is in the range from 0.15 denier to 30 denier.

18. The composition according to claim 16, wherein the fibers have a yarn count which is in the range from 0.18 denier to 18 denier.

19. The composition according to claim 1, wherein the fibers have a length L and a diameter D such that L/D is within the range from 3.5 to 2500.

20. The composition according to claim 19, wherein L/D is within the range from 5 to 500.

21. The composition according to claim 19, wherein L/D is within the range from 5 to 150.

22. The composition according to claim 1, wherein the fibers have a length ranging from 0.1 mm to 5 mm.

23. The composition according to claim 21, wherein the fibers have a length ranging from 0.2 mm to 1.6 mm.

24. The composition according to claim 1, wherein the fibers have an average diameter ranging from 2 nm to 100 μm.

25. The composition according to claim 1, wherein the fibers are present in an amount of from 0.1% to 20% relative to the total weight of the composition.

26. The composition according to claim 24, wherein the fibers are present in an amount of from 0.5% to 10% relative to the total weight of the composition.

27. The composition according to claim 1, additionally comprising a fatty phase.

28. The composition according to claim 27, wherein the fatty phase comprises at least one fatty substance selected from the group consisting of volatile and non-volatile oils that are liquid at room temperature, waxes, gums and pasty fatty substances of animal, plant, mineral and synthetic origin, and mixtures thereof.

29. The composition according to claim 27, wherein the fatty phase comprises at least one oil selected from the group consisting of perhydrosqualene, heptanoic and octanoic acid triglycerides, sunflower oil, corn oil, soybean oil, marrow oil, grapeseed oil, sesame oil, hazelnut oil, apricot oil, macadamia oil, arara oil, castor oil, avocado oil, caprylic/capric acid triglycerides, jojoba oil, Karite butter, liquid paraffins and derivatives thereof, petroleum jelly, polydecenes, hydrogenated polyisobutene, purcellin oil, isopropyl myristate, isononyl isononanoate, 2-ethylhexyl palmitate, 2-octyldodecyl stearate, 2-octyldodecyl erucate, isostearyl isostearate, isostearyl lactate, octyl hydroxystearate, octyldodecyl hydroxystearate, diisostearyl malate, triisocetyl citrate, fatty alkyl heptanoates, octanoates and decanoates, propylene glycol dioctanoate, neopentyl glycol diheptanoate, diethylene glycol diisononanoate, pentaerythritol esters, octyldodecanol, 2-butyloctanol, 2-hexyldecanol, 2-undecylpentadecanol, oleyl alcohol, volatile and non-volatile, linear and cyclic polydimethylsiloxanes (PDMSs) that are liquid at room temperature, phenyl trimethicones, phenyltrimethylsiloxydiphenylsiloxanes, diphenyl dimethicones, diphenylmethyldiphenyltrisiloxanes and 2-phenylethyl trimethylsiloxysilicates, and mixtures thereof.

30. The composition according to claim 1, additionally comprising an aqueous-phase gelling agent.

31. The composition according to claim 26, additionally comprising an aqueous-phase gelling agent.

32. The composition according to claim 30, wherein the aqueous-phase gelling agent is selected from the group consisting of xanthan gum, clays, associative polyurethanes, cellulosic thickeners and crosslinked, at least partially neutralized polyacrylic acids.

33. The composition according to claim 1, additionally comprising a particulate phase which is present in a proportion of up to 60% relative to the total weight of the composition.

34. The composition according to claim 33, wherein the particulate phase is present in a proportion of from 5% to 35% relative to the total weight of the composition.

35. The composition according to claim 1, additionally comprising at least one cosmetic or dermatological active agent.

36. The composition according to claim 1, which is in the form of a hydrophilic gel or a rigid or soft oil-in-water or water-in-oil emulsion, optionally cast as a stick or a dish.

37. The composition according to claim 1, additionally comprising at least one ingredient selected from the group consisting of antioxidants, essential oils, preserving agents, fragrances, liposoluble polymers, liquid-fatty-phase gelling agents, waxes, gums, fillers, dispersants and water-miscible compounds, and mixtures thereof.

38. The composition according to claim 1, which is in the form of a foundation, face powder or eyeshadow composition, a concealer product, a make-up product for the body, a lipstick, an eyeliner, a nail varnish, a care base or a fixing base for the lips, a dermatological product or a care product for the skin, an antisun composition or an artificial tanning composition, or a cleansing product for the skin.

39. A process for making up keratin substances comprising applying the composition of claim 1 to keratin substances.

40. A process for obtaining a homogeneous make-up, which comprises introducing into a cosmetic composition particles of an at least partially crosslinked, solid elastomeric polyorganosiloxane dispersed in an aqueous phase, and fibers.

41. The composition according to claim 1, further comprising a polyol.

42. The composition according to claim 41, wherein said polyol has an inorganic/organic balance value greater than 0.5.

43. The composition according to claim 42, wherein said polyol has an inorganic/organic balance ranging from 1 to 7.

44. The composition according to claim 43, wherein said polyol has an inorganic/organic balance ranging from 1.5 to 5.5.

45. The composition according to claim 38, wherein the composition is a foundation.

46. A care or make-up composition for keratin substances comprising from 4% to 20% pigments relative to the total weight of the composition and an aqueous phase, said aqueous phase comprising fibers and particles of an at least partially crosslinked solid elastomeric polyorganosiloxane dispersed therein.

47. The composition according to claim 46, wherein the composition comprises from 5% to 10% pigments relative to the total weight of the composition.

48. The composition according to claim 46, wherein the pigment is a mineral pigment.

49. The composition according to claim 48, wherein the mineral pigment is selected from the group consisting of titanium dioxide and zirconium oxide.

50. The composition according to claim 46, wherein the pigment is an organic pigment.

51. The composition according to claim 50, wherein the organic pigment is selected from the group consisting of carbon black, barium lake, strontium lake, calcium lake and aluminum lake.

52. The composition according to claim 1, wherein the dyestuff comprises pigments.

53. The composition according to claim 1, wherein the dyestuff comprises nacres.

54. The composition according to claim 1, wherein the dyestuff comprises fillers.

55. The composition according to claim 1, wherein the dyestuff comprises dyes.

56. The composition according to claim 1, wherein said composition is in the form of a stick.

57. The composition according to claim 56, wherein said composition is lipstick.

58. The composition according to claim 1, wherein said composition is a foundation.

59. The composition according to claim 1, wherein said composition is solid.

60. The composition according to claim 46, wherein said composition is in the form of a stick.

61. The composition according to claim 60, wherein said composition is lipstick.

62. The composition according to claim 46, wherein said composition is a foundation.

63. The composition according to claim 46, wherein said composition is solid.

* * * * *

UNITED STATES PATENT AND TRADEMARK OFFICE
CERTIFICATE OF CORRECTION

PATENT NO. : 6,689,345 B2
DATED : February 10, 2004
INVENTOR(S) : Nathalie Jager Lezer It is certified that error appears in the above-identified patent and that said Letters Patent is hereby corrected as shown below:

<u>Title page,</u>
Item [54], Title, "POLYOGANOSILOXANE" should read
-- POLYORGANOSILOXANE --.

<u>Column 12,</u>
Line 13, "82" should read -- $\mu$m --.

Signed and Sealed this

Twenty-fifth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,689,345 B2
DATED : February 10, 2004
INVENTOR(S) : Nathalie Jager Lezer It is certified that error appears in the above-identified patent and that said Letters Patent is hereby corrected as shown below:

<u>Column 14,</u>
Line 35, "20%" should read -- 25% --.

Signed and Sealed this

Twenty-seventh Day of July, 2004

JON W. DUDAS
*Acting Director of the United States Patent and Trademark Office*